United States Patent

Izuchukwu et al.

[11] Patent Number: 5,937,951
[45] Date of Patent: Aug. 17, 1999

[54] SKIN STAPLER WITH RACK AND PINION STAPLE FEED MECHANISM

[75] Inventors: John I. Izuchukwu, Loveland; Jeremy D. Jarrett, Cincinnati; Charles A. Hansford, Liberty Township; Eugene L. Timperman; Leslie M. Fugikawa, both of Cincinnati, all of Ohio

[73] Assignee: Ethicon Endo-Surgery, Inc., Cincinnati, Ohio

[21] Appl. No.: 08/897,177

[22] Filed: Jul. 18, 1997

[51] Int. Cl.⁶ .................................................. B23Q 5/00
[52] U.S. Cl. ....................... 173/176.1; 173/91; 173/175.1
[58] Field of Search ................. 227/83, 88, 89, 227/176.1, 19, 175.1, 114, 115, 116, 67

[56] References Cited

U.S. PATENT DOCUMENTS

| | | | |
|---|---|---|---|
| 3,643,851 | 2/1972 | Green et al. | 227/19 |
| 3,797,722 | 3/1974 | Bone | 227/67 |
| 4,049,179 | 9/1977 | Jenkins | 227/67 |
| 4,109,844 | 8/1978 | Becht | 227/120 |
| 4,127,227 | 11/1978 | Green | 227/83 |
| 4,179,057 | 12/1979 | Becht et al. | 227/19 |
| 4,196,836 | 4/1980 | Becht | 227/110 |
| 4,391,402 | 7/1983 | Campbell et al. | 227/121 |
| 4,406,392 | 9/1983 | Campbell et al. | 227/19 |
| 4,410,125 | 10/1983 | Noiles et al. | 227/19 |
| 4,411,378 | 10/1983 | Warman | 227/19 |
| 4,448,194 | 5/1984 | DiGiovanni et al. | 128/334 R |
| 4,493,322 | 1/1985 | Becht | 227/177.1 |
| 4,523,707 | 6/1985 | Blake, III et al. | 227/19 |
| 4,558,810 | 12/1985 | Mulhauser et al. | 227/19 |
| 4,591,086 | 5/1986 | Campbell et al. | 227/19 |
| 4,596,350 | 6/1986 | Smith et al. | 227/19 |
| 4,648,542 | 3/1987 | Fox et al. | 227/19 |
| 4,664,305 | 5/1987 | Blake, III et al. | 227/19 |
| 4,673,120 | 6/1987 | Strausburg | 227/67 |
| 4,691,853 | 9/1987 | Storace | 227/19 |
| 4,715,521 | 12/1987 | Strausburg | 227/67 |
| 4,747,531 | 5/1988 | Brinkerhoff et al. | 227/19 |
| 4,796,793 | 1/1989 | Smith et al. | 227/19 |
| 4,811,886 | 3/1989 | Murray | 227/19 |
| 4,951,860 | 8/1990 | Peters et al. | 227/177 |
| 4,971,238 | 11/1990 | Furutsu | 227/2 |
| 5,161,725 | 11/1992 | Murray et al. | 227/182 |
| 5,170,926 | 12/1992 | Ruckdeschel et al. | 227/177 |
| 5,240,164 | 8/1993 | Murray et al. | 227/175 |
| 5,251,801 | 10/1993 | Ruckdeschel et al. | 227/177 |
| 5,265,786 | 11/1993 | Heimerl et al. | 227/175 |
| 5,330,087 | 7/1994 | Murray et al. | 227/175 |
| 5,388,749 | 2/1995 | Davignon et al. | 227/67 |
| 5,433,366 | 7/1995 | Deschenes et al. | 227/67 |
| 5,465,895 | 11/1995 | Knodel et al. | 227/176 |
| 5,487,500 | 1/1996 | Knodel et al. | 227/181.1 |
| 5,738,265 | 4/1998 | Hirai et al. | 227/67 |

*Primary Examiner*—Peter Vo
*Assistant Examiner*—Matthew Luby
*Attorney, Agent, or Firm*—Louis J. Capezzuto

[57] ABSTRACT

An improved surgical stapler includes a stapler body having a driver and a magazine connected to the stapler body. The magazine includes a staple track for carrying a plurality of staples and an anvil associated with the staple track. The anvil has a staple forming surface for forming each of the staples thereon. A trigger is operatively connected to the driver for advancing the driver against the anvil so as to form the staple against the staple forming surface of the anvil. A feeder for feeding each of the staples from the staple track to the anvil is movably mounted in the magazine. A pinion is operatively connected to the trigger and is movably engaged with the feeder. An indexing member is movably engaged with the pinion such that the indexing member and the pinion advance the feeder and the staples toward the anvil upon an actuation of the trigger.

17 Claims, 10 Drawing Sheets

SKIN STAPLER WITH RACK AND PINION STAPLE FEED MECHANISM

FIELD AND BACKGROUND OF THE INVENTION

The present invention relates, in general, to tissue fastening devices and, in particular, to a new and useful wound closure device, such as a skin stapler, that allows for the multi-directional release of a staple from the device upon firing while utilizing a novel rack and pinion staple feed mechanism.

It is well established in the prior art that there are many devices that exist which utilize staples for fastening tissue. Many of these existing or known devices are directed toward closing a wound, fastening a skin incision, curing a defect in tissue or fastening a prosthetic to tissue for repairing a defect or the like.

In particular, there are a number of known prior art skin staplers that contain a multiplicity of staples and are used for closing wounds or incisions in the skin. These skin staplers are usually multi-fire instruments meaning that they contain and fire a plurality of staples. These instruments are designed to be disposable and used for a single patient only.

One known prior art skin stapler is disclosed in U.S. Pat. Nos. 4,391,402; 4,406,392 and 4,591,086 (Campbell et al.). Similar to many other known skin staplers, the stapler disclosed in the above-identified patents utilizes an L-shaped anvil. The L-shaped anvil configuration comprises an elongated leg portion and a small leg portion that is orthogonal or parallel to the elongated leg portion for providing a staple forming surface thereon. Accordingly, a former or driver is used to move parallel to the elongated leg portion in order to form a staple around the small leg portion of the anvil. In conjunction with the driver and anvil configuration and orientation, a leaf spring, which is a unitary part of the staple track, is utilized for retaining the staple stack away from the staple being formed, e.g. the distal-most staple, on the small leg portion of the anvil in order to prevent the staple stack from interfering with the forming of the distal-most staple.

Other known skin staplers are disclosed in U.S. Pat. No. 3,643,851 (Green et al.) and U.S. Pat. No. 4,127,227 (Green). Similar to the prior art devices described above, these skin staplers utilize a similar anvil having a substantially L-shaped configuration. Additionally, the driver for these stapling instruments is advanced parallel to the elongated leg portion of the anvil. Additionally, a spring ejector is located adjacent the anvil for engaging the formed staple at the crown of the staple in order to lift the staple off of the anvil by its crown after firing.

In addition to the skin staplers identified above, there are other known skin staplers which also utilize a spring ejector for ensuring that the formed staple is moved away from the anvil of the instrument. These devices are identified as follows: the PRECISE PGX™, manufactured and sold by 3M Healthcare, St. Paul, Minn.; the Davis-Geck APPOSE ULC™, manufactured and sold by American Cyanamid Company, Danbury, Conn.; VISISTAT RH™, manufactured and sold by Edward Weck and Company, Inc., Research Triangle Park, N.C.; and the Auto Suture (Cricket™, Royal™, Signet™, Concorde™, Elite™ and Multi-fire Premium™) skin stapler products, manufactured and sold by United States Surgical Corporation, Norwalk, Conn. All of these skin stapler products are available in the market and utilize a similar driver and anvil configuration such as disclosed above. These devices all utilize a driver that moves substantially parallel to the elongated leg portion of the anvil in order to form a staple across the surface of the small leg portion of the anvil. Furthermore, in all of these skin stapler devices, the staple is moved away from the anvil of the instrument through the use of a spring ejector which engages the staple at the far corners of the staple crown, i.e. at the juncture of the upper most portion of the staple leg and the corner of the staple crown. Accordingly, the staple is dislodged from the surface of the anvil by using the spring ejector to force the staple off of the anvil by its crown.

One skin stapler that utilizes a spring ejector or kick-off spring to release the staple from the skin stapler is the PROXIMATE PLUST™ Skin Stapler manufactured by Ethicon Endo-Surgery, Inc., Cincinnati, Ohio. This skin stapler utilizes a novel kick-off spring that has a tip which cams against the legs of the staple in order to eject the staple off of and away from the anvil of the stapler. This skin stapler is embodied in pending U.S. patent application Ser. No. 08/815,811 (Applicant's Docket No. END-378) filed on Mar. 12, 1997 which is incorporated herein by reference.

Additionally, the PROXIMATE PLUS™ Skin Stapler also utilizes a spring biased staple feed mechanism in order to feed each staple from the staple stack to the anvil of the stapler. This spring biased staple feed mechanism utilizes a spring coil and is embodied in U.S. Pat. No. 4,179,057 (Becht et al.) which is also incorporated herein by reference as well as embodied in the pending application identified above.

Since this staple feed mechanism is a spring coil, it is required to meet a minimum spring force threshold so that the staples can be fed to the anvil of the instrument. Accordingly, each spring coil is tested prior to instrument assembly to ensure that the spring force threshold is met.

The present invention is directed to a staple feed mechanism that eliminates the spring coil and the pre-assembly testing outlined above.

SUMMARY OF THE INVENTION

The present invention relates to tissue fastening devices which include staples, such as a skin stapler, for closing wounds, incisions or curing a defect in tissue such as fastening a prosthetic to the tissue. The present invention is a surgical stapler having a novel staple feed mechanism. The surgical stapler also allows for the multi-directional release of staples when fired.

The surgical stapler includes a stapler body having a driver and a magazine connected to the stapler body. The magazine includes a staple track for carrying a plurality of staples and an anvil associated with the staple track. The anvil has a staple forming surface for forming each of the staples thereon. A trigger is operatively connected to the driver for advancing the driver against the anvil so as to form the staple against the staple forming surface of the anvil. A feeder for feeding each of the staples from the staple track to the anvil that is, in turn movably mounted in the magazine. A pinion is operatively connected to the trigger and is movably engaged with the feeder. An indexing member is movably engaged with the pinion such that the indexing member and the pinion advance the feeder and the staples toward the anvil upon an actuation of the trigger.

A kick-off spring is positioned beneath and substantially parallel to the staple track and to the anvil. The kick-off spring has a deflectable tip which is deflected away from the anvil and engages the surfaces of the staple legs. The deflectable tip engages the inner surfaces of the staple legs when the trigger is moved from a pre-fire position to a staple forming position. As the trigger is released from its staple forming position, the kick-off spring ejects the staple off of and away from the anvil by disengaging the staple legs with the deflectable tip. This disengagement occurs as the deflectable tip moves in an upward direction camming along the surface of the staple legs toward the staple crown.

The ejection of the staple from the anvil by the deflectable tip is an effective way for releasing the staple from the stapler since the staple is rotated away from the anvil due to the camming action of the deflectable tip on the inner surface of the staple legs. The rotatable release of the staple permits the stapler to be used and advanced in a forward linear direction and eliminates the possibility of the fired staple from re-entering the stapler after firing thus avoiding any possible jam of the instrument.

It is an object of the present invention to provide a surgical stapler that has a staple feed mechanism that is indexed along a pre-determined feeding path.

It is another object of the present invention to provide a surgical stapler with an improved staple feed mechanism that is cost effective and easy to manufacture.

It is another object of the present invention to provide a surgical stapler that allows for the multi-directional release of the staple upon firing.

It is another object of the present invention to provide a surgical stapler that utilizes a kick-off spring to eject the staple from the stapler in a manner which prevents re-entering of the staple into the instrument and avoids jamming or misfiring.

It is another object of the present invention to provide a surgical stapler with a kick-off spring that is cost effective and easy to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
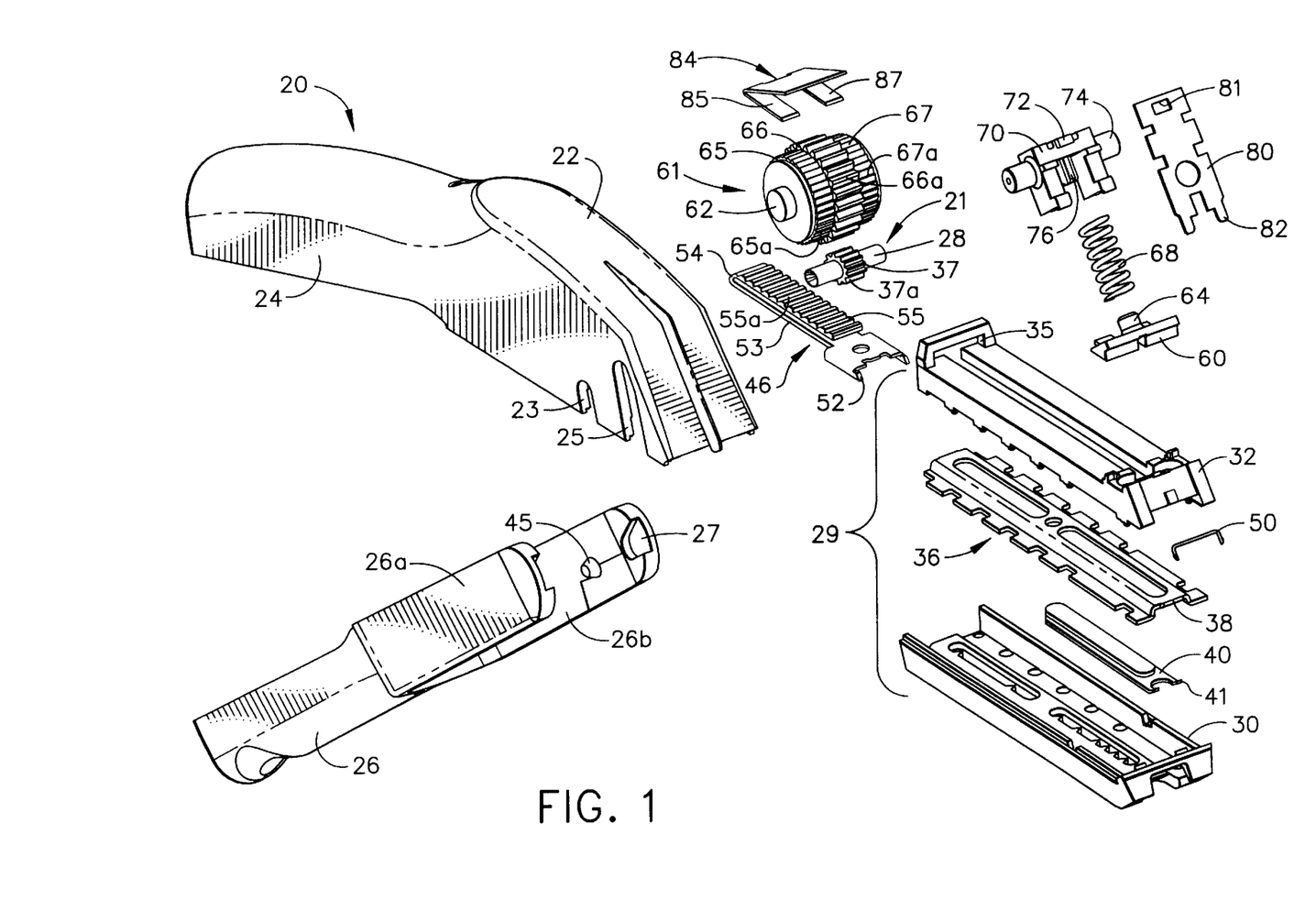
FIG. 1 is an exploded perspective view of a preferred embodiment of an improved surgical stapler employing a preferred embodiment of a rack and pinion staple feed mechanism.

As shown in FIG. 1, the present invention is a tissue fastening device, such as a surgical stapler 20 which is used for the closing of wounds, incisions, defects in tissue or the fastening of a prosthetic to tissue.

The stapler 20 is generally used as a skin stapler for the uses identified above. The stapler 20 comprises a stapler body 22 having an ergonomic handle 24 which is integral with the body 22. A trigger 26 is operatively connected to the body 22 as best illustrated in FIG. 1. The stapler 20 is similar to the stapler described in U.S. Pat. No. 4,179,057 (Becht et al.) which has been incorporated herein by reference. Although not identified by the same name or same reference numeral, some of the features of the stapler 20 according to the present invention are similar in function to those described in U.S. Pat. No. 4,179,057 and are well within the purview of one of ordinary skill in the surgical field.

Figure 21:
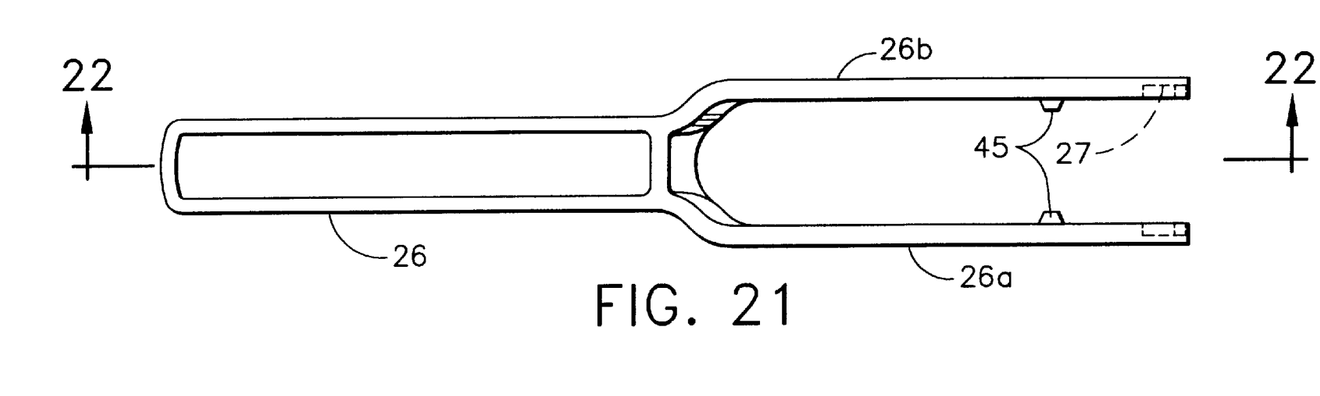
FIG. 21 is a top view of the trigger of FIG. 1.
Figure 22:
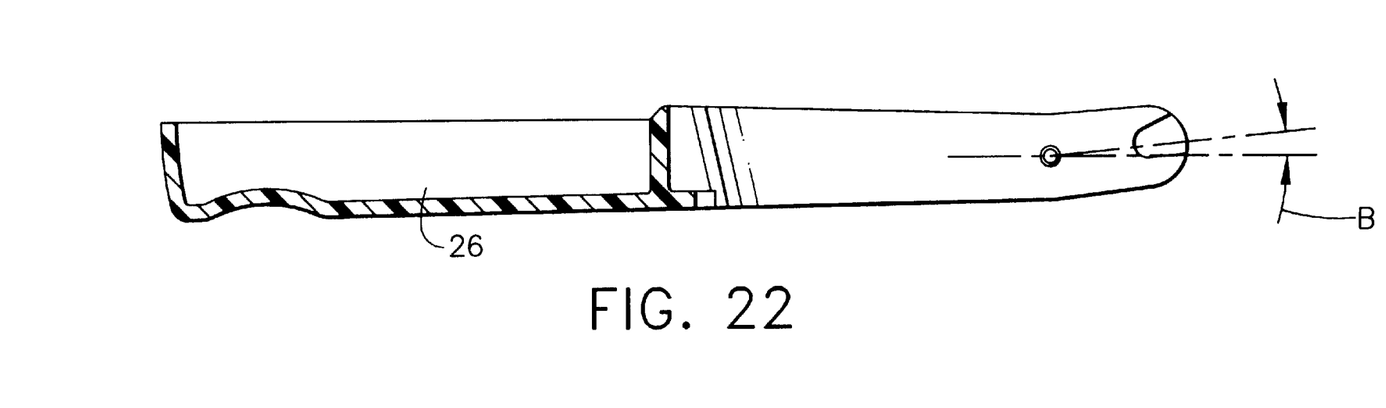
FIG. 22 is a view taken along line 22—22 of FIG. 21.

As best illustrated in FIG. 1, the stapler body 22 includes a pivot bar recess 23 and an actuator recess 25 adjacent to each other at the distal end of the stapler body 22. As shown in FIGS. 21 and 22, the actuating trigger 26 includes two arms 26a and 26b which define a substantially Y-shaped configuration for the trigger 26 and is rotatably connected to the stapler body 22 (FIG. 1). The trigger arms 26a and 26b include a tapered pin 45 positioned on an inner surface of the arms 26a and 26b. The tapered pins 45 have a truncated conical shape. The trigger arms 26a and 26b also include a trunnion recess 27 at the distal end of the arms 26a and 26b.

Figure 14:
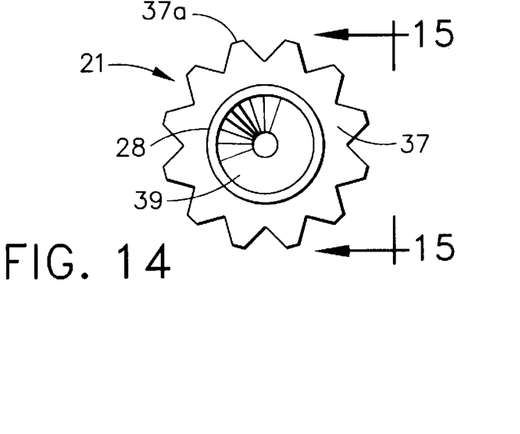
FIG. 14 is a right side elevational view of the pinion gear of the preferred rack and pinion staple feed mechanism.
Figure 15:
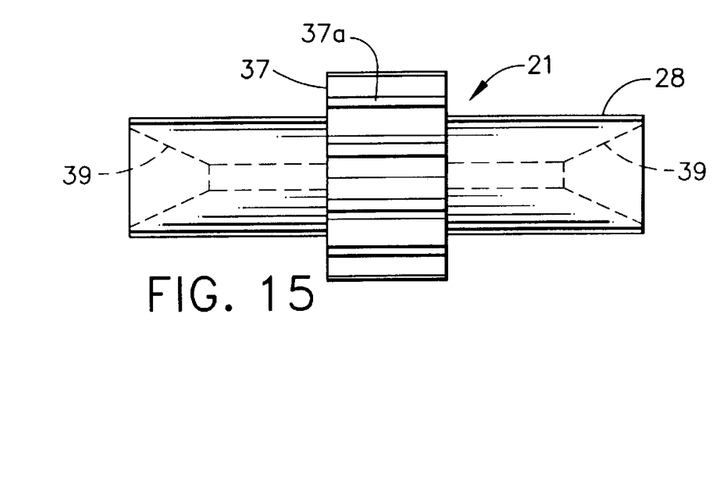
FIG. 15 is a view taken along line 15—15 of FIG. 14.

As best shown in FIGS. 14 and 15, a pinion assembly, generally designated 21, includes a pinion shaft 28 and a pinion 37 centrally and circumferentially positioned on the pinion shaft 28. The pinion 37 includes a plurality of circumferentially arranged teeth 37a.

Figure 5:
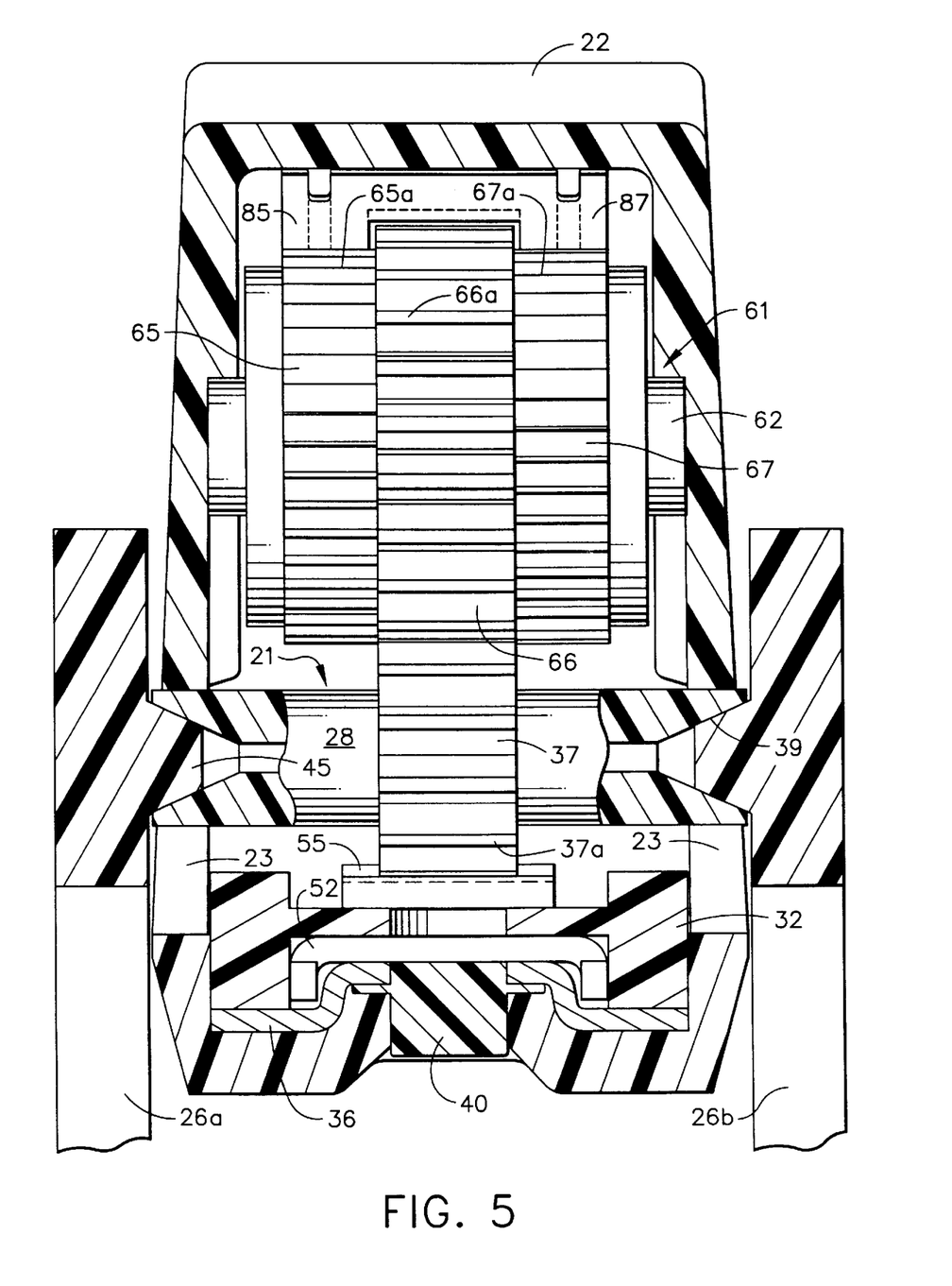
FIG. 5 is a section view taken along line 5—5 of FIG. 4.

Additionally, the pinion shaft 28 has a truncated conical section or brake 39 hollowed out from each end of the pinion shaft 28. The pinion assembly 21 is positioned between the trigger arms 26a and 26b such that pins 45 are positioned within the brakes 39. The pinion shaft 28 is seated in the pivot bar recess 23 of the stapler body 22 as illustrated in FIG. 5.

The stapler 20 also includes an actuator 70 having a driver detent 72 and a trunnion 74 located at opposite ends of the actuator 70 as shown in FIG. 1. The trunnions 74 are received in the trunnion recess 27 of the trigger arms 26a and 26b. Additionally, the trunnions 74 are received in the actuator recess 25 of the stapler body 22. Accordingly, the above-mentioned arrangement allows for the trigger 26 to be rotated in a direction R from a pre-fire position P (FIG. 3) to a staple forming position F (FIG. 6) upon the depression of the trigger 26 toward the stapler handle 24. When depressed or squeezed by the surgeon, the trigger 26 will be moved or rotated in direction R toward the handle 24 since the trunnions 74 of the actuator 70 are movable in the actuator recess 25 of the stapler body 22 and the pinion shaft 28 is movable in the pivot bar recess 23 of the stapler body 22.

A driver 80 having a detent aperture 81 located at the proximal end of the driver 80 is connected to the driver detent 72 of the actuator 70. The driver 80 also includes driver tines 82 which are located at the distal end of the driver 80. The actuator 70 includes an upper spring post 76 for receiving a return spring 68. The return spring 68 is also in engagement with a spring seat 60 having a lower spring post 64 for receiving the spring 68 thereon. Accordingly, the return spring 68 is resiliently positioned between the upper spring post 76 of the actuator 70 and the lower spring post 64 of the spring seat 60.

A magazine 29 including a lower magazine section 30 and an upper magazine section 32 is connected to the stapler body 22 as shown in FIGS. 1, 3, 6 and 8. The upper magazine section 32 includes a proximal opening 35 located at the proximal end of the upper magazine section 32.

Figures 3, 4:
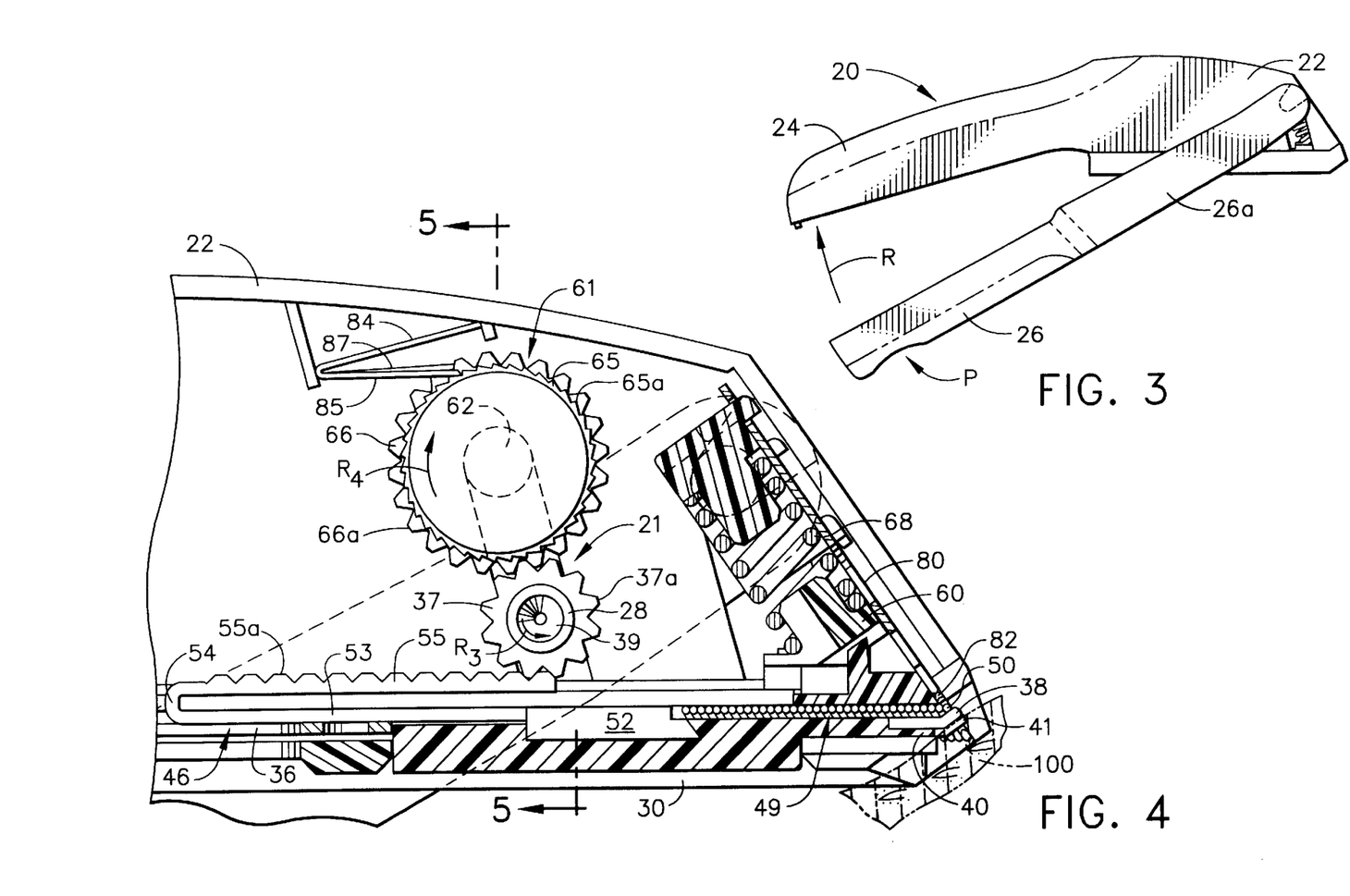
FIG. 3 is a side elevation view of the stapler of FIG. 1 in a pre-fire position.
FIG. 4 is an enlarged side elevation view in section of a distal portion of the preferred stapler in the pre-fire position shown in FIG. 3.

The magazine 29 also includes a staple track 36 for carrying a plurality of staples or a staple stack 49 (FIG. 4). The staple track 36 includes an anvil 38 located at the distal-most portion of the staple track 36. The anvil 38 provides a surface for the formation of a staple 50 thereabout upon the firing of the stapler 20.

Figure 16:
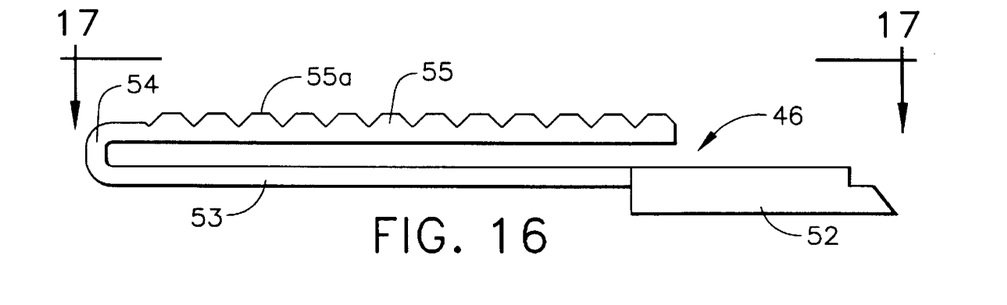
FIG. 16 is a side elevational view of a staple feeder of the preferred rack and pinion staple feed mechanism.
Figure 17:
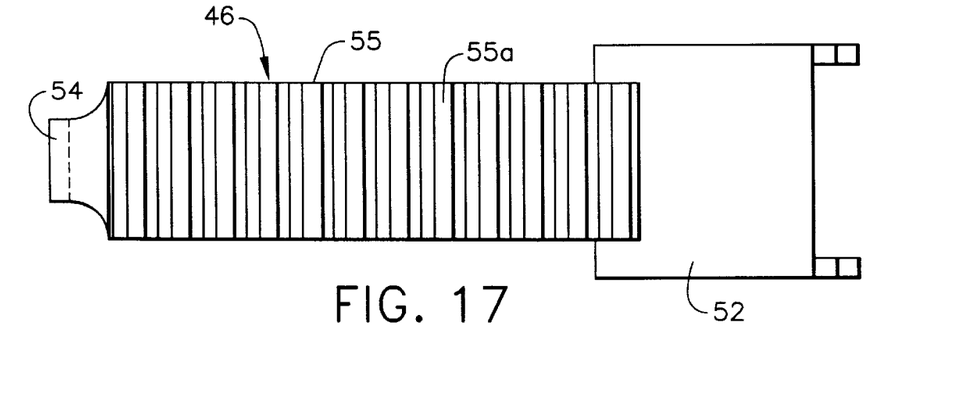
FIG. 17 is a view taken along line 17—17 of FIG. 16.
Figure 18:
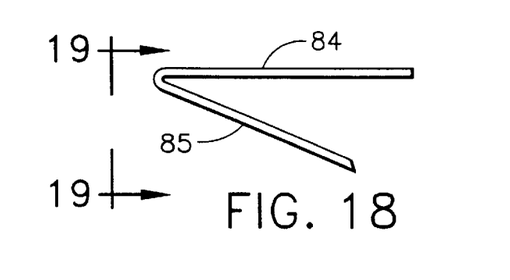
FIG. 18 is a side elevational view of a twin pall member of the preferred rack and pinion staple feed mechanism.
Figure 19:
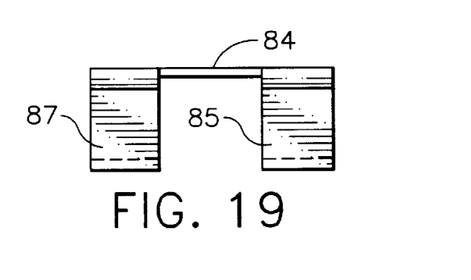
FIG. 19 is a view taken along line 19—19 of FIG. 18.
Figure 20:
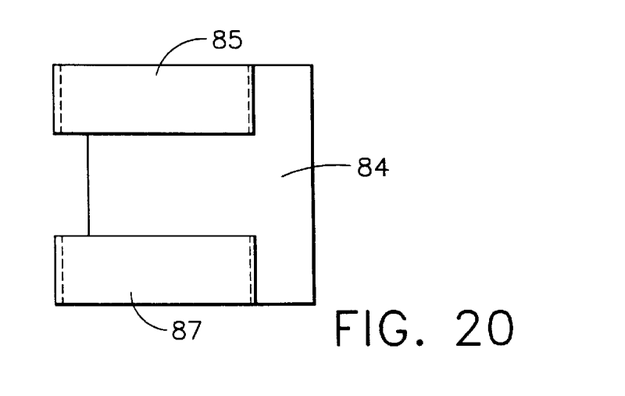
FIG. 20 is a bottom view of the twin pall member of FIG. 18.

As shown in FIGS. 1, 16 and 17, the stapler 20 also includes a feeder 46 having a feeder base 53 and a feeder shoe 52 at a distal end of the feeder base 53. The feeder 46 also includes a return leaf 54 which is a C-shaped section extending from the proximal end of the feeder base 53 to a rack 55. The rack 55 is spaced away from and positioned parallel to the feeder base 53. The rack has a plurality of teeth 55a on an upper surface of the rack 55. The pinion teeth 37a (FIG. 4) of the pinion 37 are movably engagable with the rack teeth 55a of the rack 55.

Figures 6, 7:
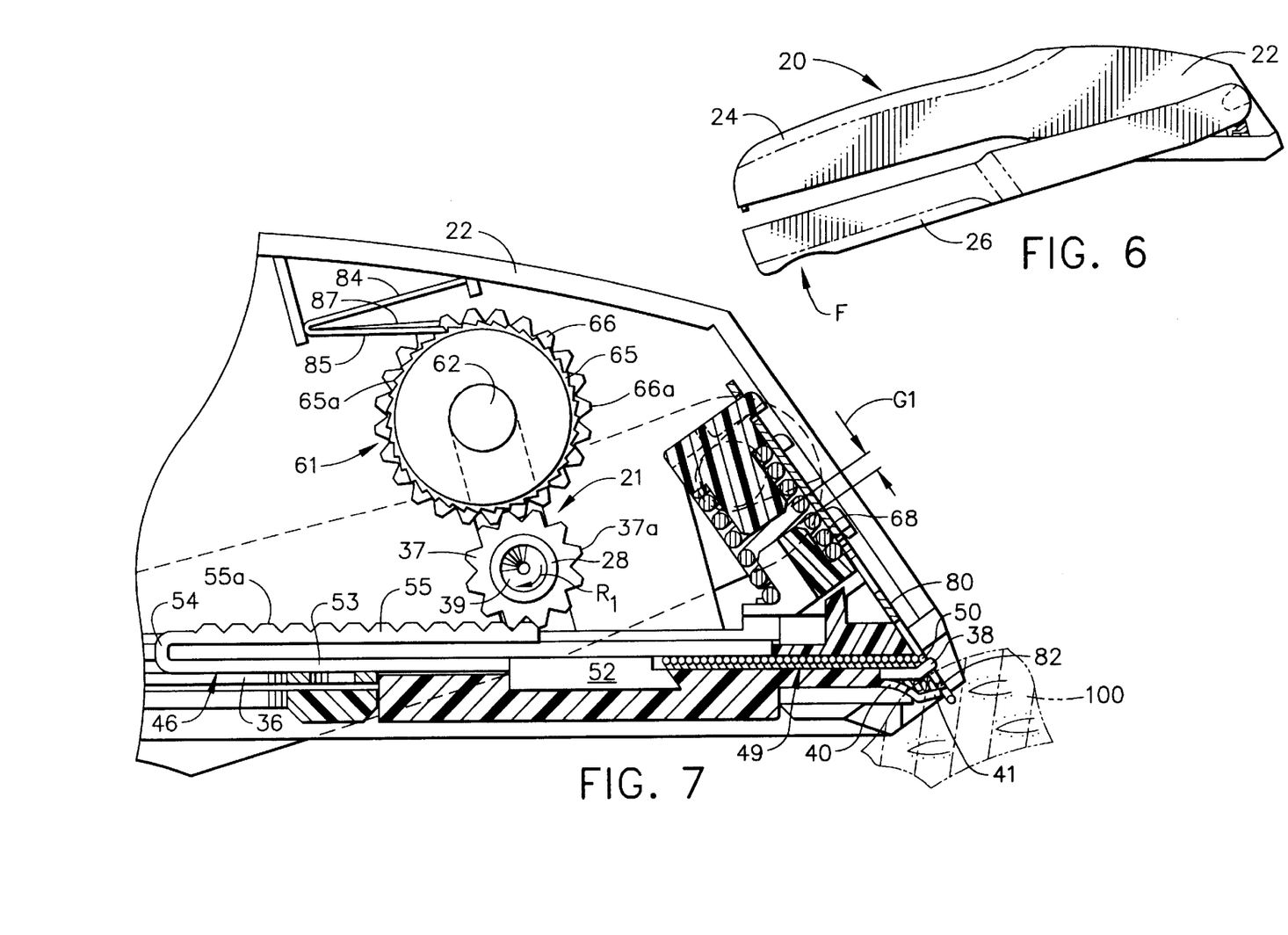
FIG. 6 is a side elevation view of the stapler of FIG. 1 with the trigger fully depressed to a staple forming position in order to form a staple.
FIG. 7 is an enlarged side elevation view in section of the distal portion of the preferred stapler in the staple forming position shown in FIG. 6.
Figures 8, 9:
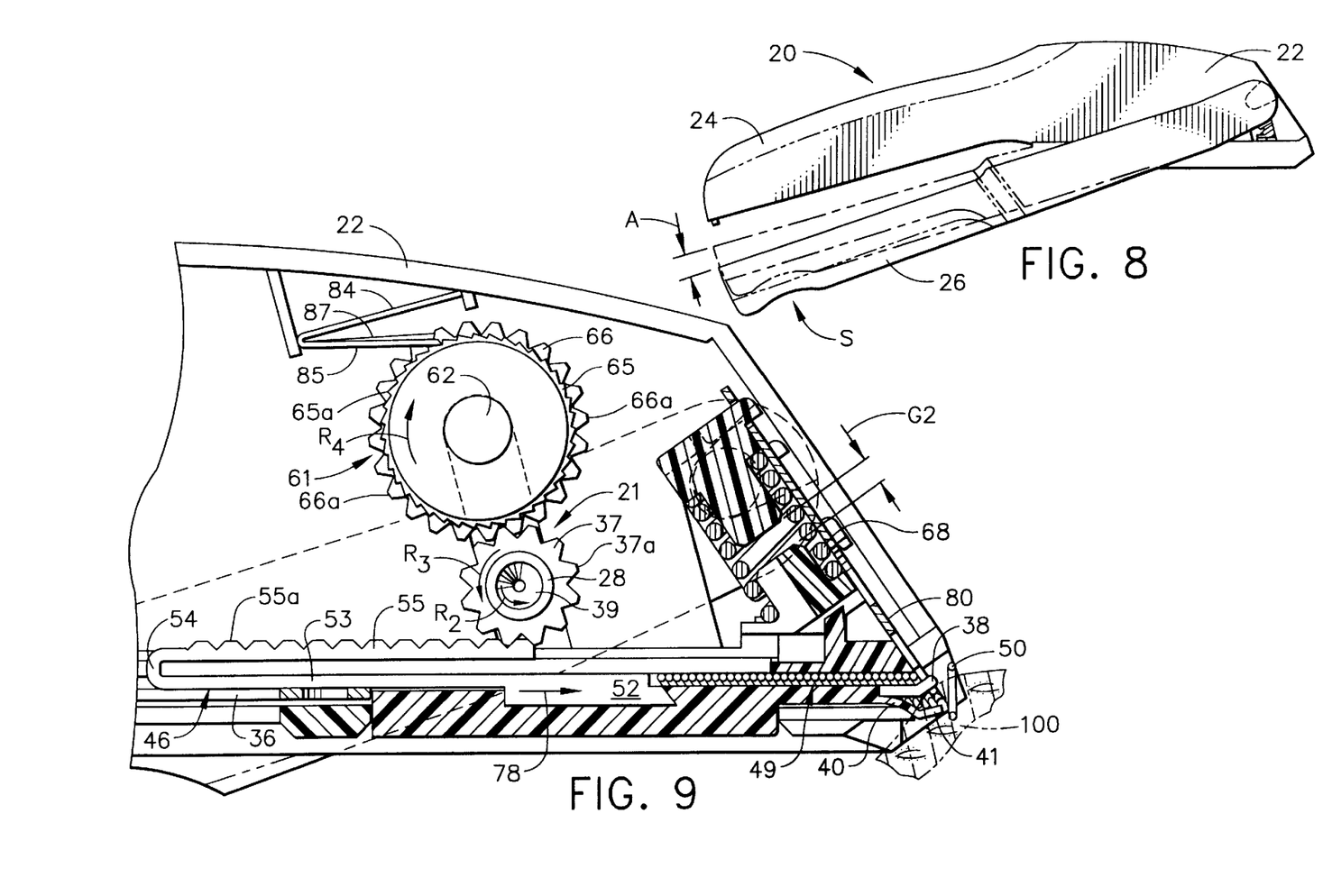
FIG. 8 is a side elevation view of the stapler of FIG. 1 with the trigger released through a trigger return angle to a staple release position to permit the formed staple to leave the stapler.
FIG. 9 is an enlarged side elevation view in section of the distal portion of the preferred stapler in the staple release position shown in FIG. 8 wherein the driver is still in place preventing the advancement of the next staple to the anvil.

The feeder 46 is movably positioned on the staple track 36 with the feeder base 53 and feeder shoe 52 movable along the upper surface of the staple track 36 to the anvil 38. The feeder return leaf 54 extends through the proximal opening 35 of the upper magazine section 32. The rack 55 is movable along the upper outer surface of the upper magazine section 32. As best illustrated in FIGS. 4, 7 and 9, the staple stack 49 is fed one staple at a time by the feeder shoe 52 of the feeder 46 along the staple track 36 to the anvil 38.

The magazine 29 also includes a kick-off spring 40 which is positioned beneath the staple track 36 and above the lower magazine section 30. The kick-off spring 40 can be made of any material, but is preferably made of a plastic material. The kick-off spring 40 has a deflectable tip 41 for contacting the staple 50 at the anvil for releasing the staple 50 away from the anvil 38 once the staple 50 is formed. Although the kick-off spring 40 is shown and described as a separate component, it is well within the ability of one of ordinary skill in the surgical field to utilize a kick-off spring that is integral with either the staple track 36 or the lower magazine section 30.

When in use, the stapler 20 is placed against tissue 100 (FIG. 7) at a position where the surgeon desires to place the staple 50. Upon positioning the stapler 20, the surgeon employs a firing sequence using the stapler 20 as best illustrated in FIGS. 3, 4, 6, 7, 8, 9 and 11. FIG. 4 shows the stapler 20 in its pre-fire position P (FIG. 3) wherein the lead staple 50 is positioned on the anvil 38. The driver tines 82 of the driver 80 are positioned above the lead staple 50 and are positioned a short distance from the lead staple 50 defining a gap therebetween. The tip 41 of the kick-off spring 40 is positioned flush against the anvil 38 at the under side of the anvil 38.

As the trigger 26 is depressed and rotated in direction R toward the handle 24 of the stapler 20 in an upward direction as indicated in FIG. 3, the driver 80 is advanced toward the lead staple 50 and the anvil 38 such that the driver tines 82 contact the lead staple 50 and begin the staple forming process. As the driver tines 82 are advanced in a downward direction, the lead staple 50 is formed.

Figure 12:
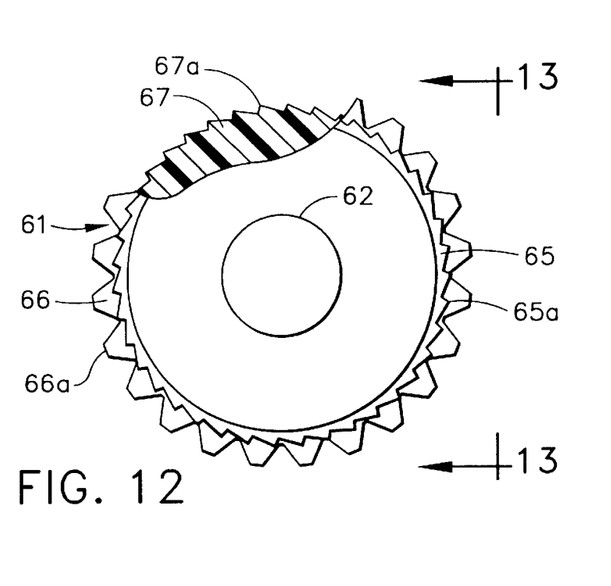
FIG. 12 is a right side elevational view of the indexing wheel partially cut away.
Figure 13:
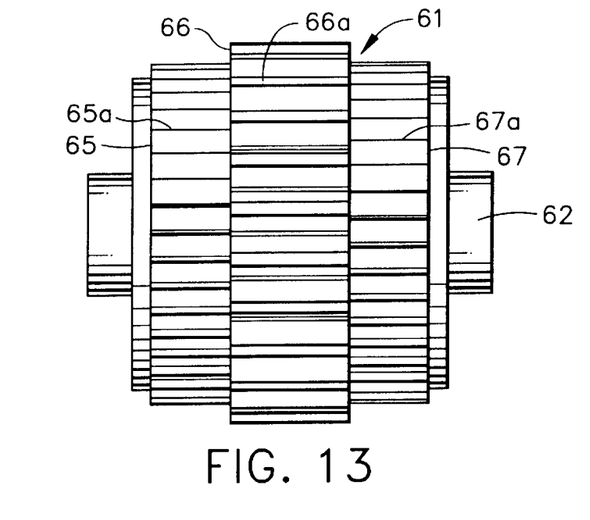
FIG. 13 is a view taken along line 13—13 of FIG. 12.

As best illustrated in FIGS. 1, 12 and 13, the stapler 20 also includes an indexing wheel 61. The indexing wheel 61 has a transfer gear 66 centrally positioned and circumferentially arranged on an indexing shaft 62. The transfer gear 66 includes a plurality of circumferentially arranged teeth 66a. The transfer gear teeth 66a are movably engaged with the pinion teeth 37a of the pinion 37.

Figure 10:
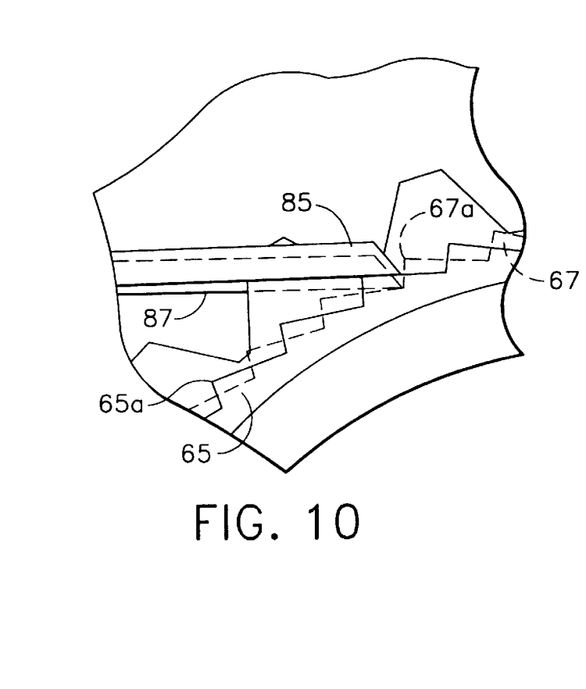
FIG. 10 is a fragmentary and enlarged side elevational view of a portion of an indexing wheel of the rack and pinion staple feed mechanism.
Figure 11:
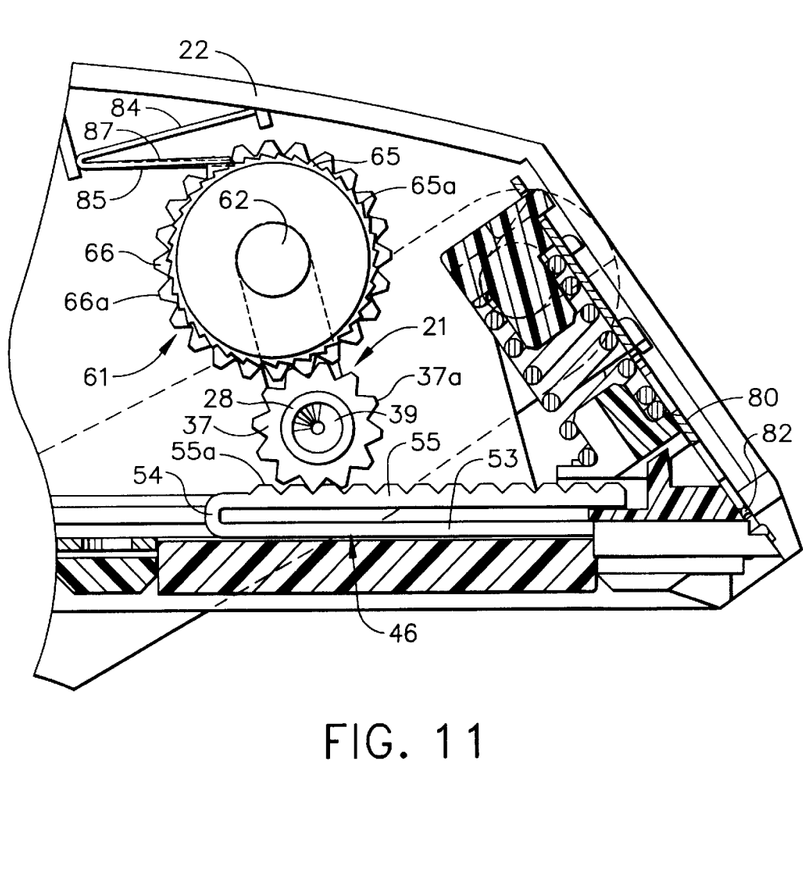
FIG. 11 is an enlarged side elevation view in section of the distal portion of the preferred stapler when the stapler has completed firing all of its staples and is empty.

A first side ratchet 65 and a second side ratchet 67 are circumferentially arranged on the indexing shaft 62 and laterally positioned on each side of the transfer gear 66. The first side ratchet 65 and the second side ratchet 67 have a plurality of circumferentially arranged teeth 65a and 67a respectively. As best shown in FIG. 10, the first side ratchet teeth 65a are offset from the second side ratchet teeth 67a. Thus, the first side ratchet teeth 65a are staggered with respect to the second side ratchet teeth 67a.

Figure 2:
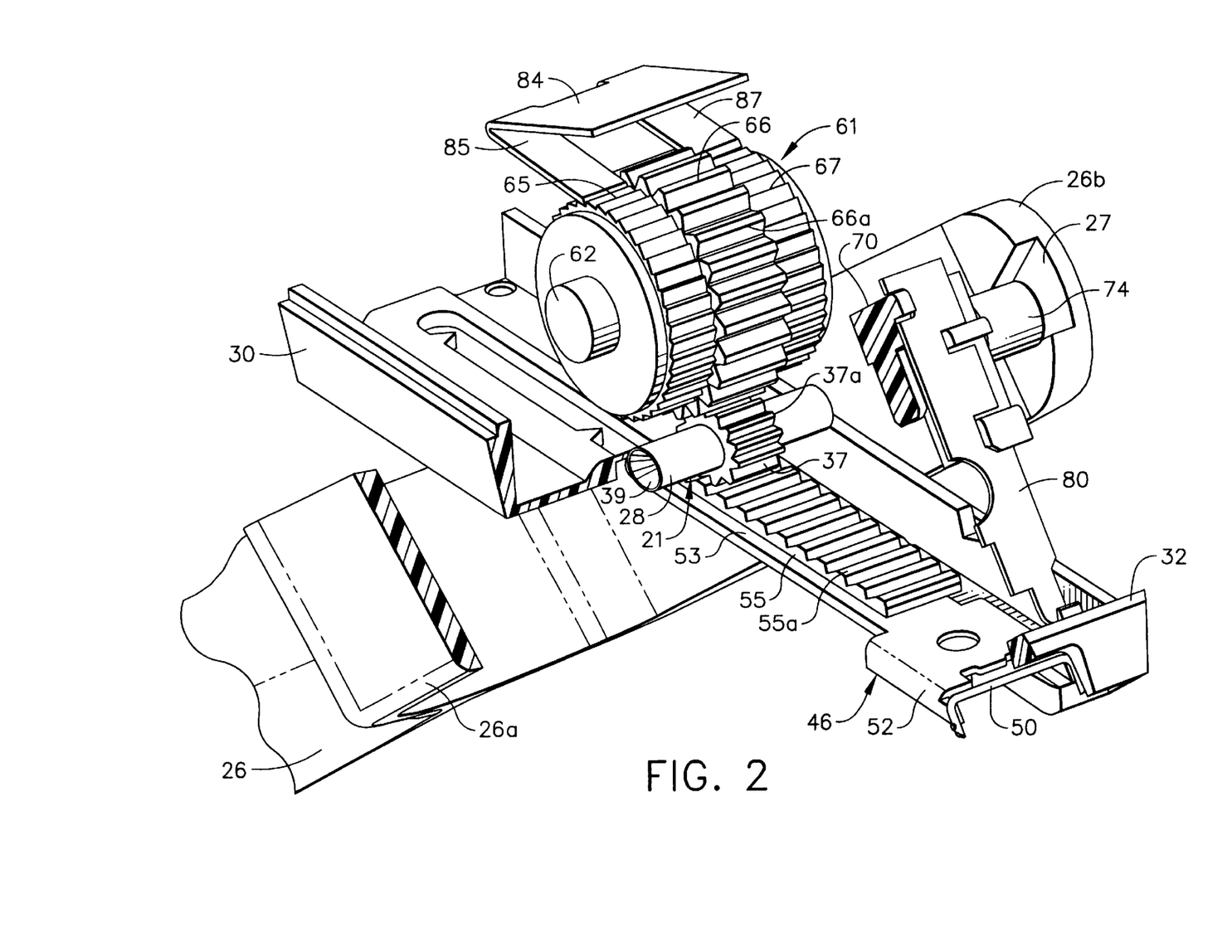
FIG. 2 is an enlarged and fragmentary perspective view of the surgical stapler of FIG. 1 with portions of the assembly removed and cut away.

As shown in FIGS. 1, 18, 19 and 20, the stapler 20 also includes a twin pall member 84 having a first side pall 85 and a second side pall 87. The twin pall member 84 is fixed within the stapler body 22 (FIGS. 7, 9 and 11) and is arranged such that the first side pall 85 is in contact with the first side ratchet 65 and the second side pall 87 is in contact with second side ratchet 67 as illustrated in FIG. 2. As will be described in better detail below, the side pall members 85 and 87 of the twin pall member 84 are movably engaged with the side ratchets 65 and 67, respectively, of the indexing wheel 61.

As the trigger 26 is being rotated in direction R toward the handle 24 to the staple forming position F (FIG. 6), the tapered pins 45 slidably move or slip within the brakes 39 in the direction indicated by rotation arrow $R_1$, as illustrated in FIG. 7. The slippage of the pins 45 within the brakes 39 is due to the matching truncated conical configuration of the pins 45 and the brakes 39. Since the pins 45 slip within the brakes 39 during the initial trigger rotation R moving toward the staple forming position F, the pinion 37 and the indexing wheel 61 remain stationary. The position of the pinion 37 and the indexing wheel 61 remain stationary initially because one of either the first side pall 85 or the second side pall 87 are contacting directly against or blocking either the first side ratchet teeth 65a or the second side ratchet teeth 67a respectively. Since the ratchet teeth 65a and 67a are staggered with respect to each, only one of the first side pall 85 or the second side pall 87 will provide the initial blocking action with respect to desired or potential movement of the pinion 37 and the indexing wheel 61. This blocking action causes the pins 45 to slip within the brakes 39 initially.

Without the blocking action provided by the twin pall member 84, the pinion 37 would rotate in a clockwise direction and the indexing wheel 61 would rotate in a counterclockwise direction.

Once the trigger 26 has reached the staple forming position F (FIG. 6), the lead staple 50 is completely formed around the anvil 38 by the driver tines 82 while fixed in the tissue 100 and the kick-off spring tip 41 is fully deflected (FIG. 7).

As soon as the trigger 26 is permitted to return from the staple forming position F (FIG. 6) to the staple pre-fire position P (FIG. 3), the pinion 37 will attempt to move in a counterclockwise rotation direction $R_3$ and the indexing wheel 61 will attempt to move in clockwise direction $R_4$. This respective movement would draw the feeder 46 distally toward the anvil 38 due to the engagement of the pinion teeth 37a with the rack teeth 55a. Initially, both the pinion 37 and the indexing wheel are prevented from moving in direction $R_3$ and $R_4$ respectively because the driver 80 blocks the advancement of the staple stack 49 and feeder 46. Accordingly, the brake 39 slips in a counterclockwise rotation direction $R_2$ up until the trigger moves through a trigger return angle A (FIGS. 8 and 9).

It is only until the trigger moved through the trigger return angle A, that the driver 80 is retracted to its original position due to the release of the compression forces exerted by the spring 68. Upon moving through trigger return angle A, the staple 50 is released from the stapler 20 by being lifted off of and away from the anvil 38 into the tissue 100 by the return action of the deflected kick-off spring tip 41 as the trigger reaches a staple release position S as shown in FIG. 8. Thus, through the return action of the kick-off spring tip 41, the staple 50 is sufficiently ejected from the stapler 20 in a manner which allows for the multi-directional release of the staple 50 thereby permitting the stapler 20 to be moved distally upon subsequent firings in a forward, distal direction from the surgeon.

After the trigger 26 moves through angle A and the trigger has reached the staple release position S, the brake 39 no longer slips and will hold the pinion 37 such that the pinion 37 is permitted to rotate in direction $R_3$. In turn, the indexing wheel will rotate in direction $R_4$. The rotation of the pinion 37 advances the feeder 46 and the staple stack 49 distally in a staple feed direction 78 until the next lead staple 50 is positioned on the anvil 38.

At this point, the indexing wheel 61 is permitted to rotate in direction $R_4$ far enough until either one of the first side pall 85 or the second side pall 87 springs into engagement behind the first side ratchet teeth 65a or the second side ratchet teeth 67a respectively. Since the ratchet teeth 65a and 67a are offset, each pall 85 and 87 respectively will alternate blocking movement of the indexing wheel 61 (FIG. 10) upon sequential actuations of the trigger 26.

Once one of the pall members 85 or 87 blocks the movement of the indexing wheel 61 opposite direction $R_4$, the tapered pins 45 will slip in the counterclockwise direction $R_2$ up until the trigger 26 is returned to its original pre-fire position P (FIG. 3).

Additionally, the relationship of the pall members 85 and 87 in conjunction with the ratchet teeth 65a and 67a along with the relationship between the transfer gear teeth 66a, pinion teeth 37a and the rack teeth 55a ensures that the staple stack 49 is advanced in the staple feed direction 78 a distance of only one staple, e.g. a distance which permits the next lead staple 50 to be advanced onto the anvil 38 aligned directly beneath the driver 80.

Although this invention has been described in connection with its most preferred embodiments, it will become readily apparent to those reviewing this detailed specification that numerous additional embodiments fall well within the scope and spirit of the claimed invention as set forth in the claims which appear below.

What is claimed is:

1. An improved surgical stapler including a stapler body having a driver, a magazine connected to said stapler body, said magazine including a staple track for carrying a plurality of staples, an anvil associated with said staple track and having a staple forming surface for forming each of said staples thereon, and a trigger operatively connected to said driver for advancing said driver against said anvil so as to form said staple against said staple forming surface of said anvil, wherein the improvement comprises:

a feeder movably mounted in said magazine for feeding each of said staples from said staple track to said anvil;

a pinion operatively connected to said trigger, said pinion being movably engaged with said feeder;

an indexing member movably engaged with said pinion, wherein said indexing member and said pinion advance said feeder and said staples toward said anvil upon an actuation of said trigger, wherein said indexing member includes a first ratchet and a second ratchet, wherein said first ratchet includes first ratchet teeth and said second ratchet includes second ratchet teeth, and wherein said first ratchet teeth and said second ratchet teeth are off-set from each other.

2. The surgical stapler according to claim 1, further including a pall member movably engaged to said indexing member.

3. The surgical stapler according to claim 2, wherein the pall member includes a first pall and a second pall, said first pall being movably engaged with said first ratchet teeth of said first ratchet and said second pall being movably engaged with said second ratchet teeth of said second ratchet.

4. The surgical stapler according to claim 2, including a brake operatively connected to said pinion and said trigger.

5. The surgical stapler according to claim 4, wherein said trigger includes at least one pin positioned in said brake.

6. The surgical stapler according to claim 5, including a kick-off spring positioned adjacent said anvil for contacting a formed staple and ejecting said formed staple away from said anvil.

7. The surgical stapler according to claim 6, wherein said trigger includes a pair of trigger arms.

8. The surgical stapler according to claim 7, wherein each trigger arm includes a pin, said pins being positioned within said brake.

9. The surgical stapler according to claim 8, wherein said feeder includes a rack.

10. The surgical stapler according to claim 9, wherein said rack is positioned outside of said magazine.

11. The surgical stapler according to claim 10, wherein said feeder is advanced in a distal direction toward said anvil.

12. The surgical stapler according to claim 11, wherein said trigger is movable from a pre-fire position to a staple forming position.

13. The surgical stapler according to claim 12, wherein said trigger pin slidably moves in said brake as said trigger is moved from said pre-fire position to said staple forming position.

14. The surgical stapler according to claim 13, wherein said trigger is movable from said staple forming position to said pre-fire position through a trigger return angle.

15. The surgical stapler according to claim 14, wherein said pinion is rotatable in a counterclockwise direction when said trigger is moved through said trigger return angle.

16. The surgical stapler according to claim 15, wherein said indexing member is rotatable in a clockwise direction when said trigger is moved through said trigger return angle.

17. The surgical stapler according to claim 16, wherein said first pall and said second pall alternatively prevent movement of said indexing member upon sequential actuations of said trigger.

* * * * *